US011925183B2

(12) United States Patent
Chen et al.

(10) Patent No.: US 11,925,183 B2
(45) Date of Patent: Mar. 12, 2024

(54) STATIC CT DETECTION DEVICE

(71) Applicants: Tsinghua University, Beijing (CN); Nuctech Company Limited, Beijing (CN)

(72) Inventors: Zhiqiang Chen, Beijing (CN); Li Zhang, Beijing (CN); Qingping Huang, Beijing (CN); Yong Zhou, Beijing (CN); Hui Ding, Beijing (CN); Chao Ji, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 93 days.

(21) Appl. No.: 17/661,257

(22) Filed: Apr. 28, 2022

(65) Prior Publication Data
US 2022/0357288 A1    Nov. 10, 2022

(30) Foreign Application Priority Data

May 7, 2021 (CN) .......................... 202110496380.2

(51) Int. Cl.
*G01N 23/046* (2018.01)
*A22B 5/00* (2006.01)
(Continued)

(52) U.S. Cl.
CPC ........... *A22B 5/007* (2013.01); *G01N 23/046* (2013.01); *G01N 23/083* (2013.01); *G01N 23/18* (2013.01);
(Continued)

(58) Field of Classification Search
None
See application file for complete search history.

(56) References Cited

U.S. PATENT DOCUMENTS 6,661,867 B2 * 12/2003 Mario .................... G01V 5/005
378/57
7,072,440 B2 * 7/2006 Mario .................. G01V 5/0025
378/57
(Continued)

FOREIGN PATENT DOCUMENTS

CN    100409001 C    8/2008
CN    201788151 U    4/2011
(Continued)

OTHER PUBLICATIONS

"International Application No. PCT/CN2022/071627, International Search Report dated Mar. 29, 2022", (dated Mar. 29, 2022), 12 pgs.

*Primary Examiner* — Thomas R Artman
(74) *Attorney, Agent, or Firm* — Schwegman Lundburg & Woessner. P.A.

(57) ABSTRACT

The present disclosure relates to a static CT detection device, including: a shielding body, formed with a detection channel through which an object under detection can pass; a ray source, emitting rays for detecting the object under detection when the object under detection passes through the detection channel; and a detector, for acquiring the rays emitted by the ray source and having passed through the detection channel, wherein the shielding body is formed with an opening portion, and the opening portion extends from an inlet of the detection channel to an outlet of the detection channel.

12 Claims, 3 Drawing Sheets

(51) Int. Cl.
   *G01N 23/083*   (2018.01)
   *G01N 23/18*    (2018.01)
   *G01N 33/12*    (2006.01)

(52) U.S. Cl.
   CPC ..... *G01N 33/12* (2013.01); *G01N 2223/1016* (2013.01); *G01N 2223/204* (2013.01); *G01N 2223/30* (2013.01); *G01N 2223/3307* (2013.01); *G01N 2223/3308* (2013.01); *G01N 2223/419* (2013.01); *G01N 2223/5015* (2013.01); *G01N 2223/618* (2013.01); *G01N 2223/643* (2013.01)

(56) References Cited

U.S. PATENT DOCUMENTS

| | | | |
|---|---|---|---|
| 9,513,234 B2* | 12/2016 | Taniguchi | A22C 17/0093 |
| 2003/0076924 A1 | 4/2003 | Mario et al. | |
| 2005/0089140 A1* | 4/2005 | Mario | G01N 23/046 |
| | | | 378/57 |
| 2014/0376693 A1* | 12/2014 | Taniguchi | A22B 5/0035 |
| | | | 378/62 |
| 2020/0400561 A1 | 12/2020 | Bringewatt et al. | |
| 2021/0041378 A1 | 2/2021 | Morton | |
| 2022/0357288 A1* | 11/2022 | Chen | G01N 23/083 |

FOREIGN PATENT DOCUMENTS

| | | |
|---|---|---|
| CN | 113514482 A | 10/2021 |
| WO | WO-2008010732 A1 | 1/2008 |
| WO | WO-2020190153 A1 | 9/2020 |

\* cited by examiner

STATIC CT DETECTION DEVICE

CROSS REFERENCES TO RELATED APPLICATION

The present application claims priority to Chinese Patent Application No. 202110496380.2, filed on May 7, 2021, which is hereby incorporated by reference in its entirety.

TECHNICAL FIELD

The present disclosure relates to CT (Computed Tomography) detection device, in particular to a static CT detection device.

BACKGROUND

In the existing CT detection device, in order to prevent rays from being radiated out, a detection channel is formed and surrounded by a shielding body, and by means of a conveying belt passing through the detection channel, an object under detection is conveyed into the detection channel and is detected. In the above case, the operation of moving the object under detection onto the conveying belt is required.

SUMMARY

The present disclosure provides a static CT detection device.

One aspect of the present disclosure relates to a static CT detection device, including: a shielding body, formed with a detection channel through which an object under detection can pass; a ray source, emitting rays for detecting the object under detection when the object under detection passes through the detection channel; and a detector, for acquiring the rays emitted by the ray source and having passed through the detection channel, wherein the shielding body is formed with an opening portion, and the opening portion extends from an inlet of the detection channel to an outlet of the detection channel.

DETAILED DESCRIPTION

Figure 1:
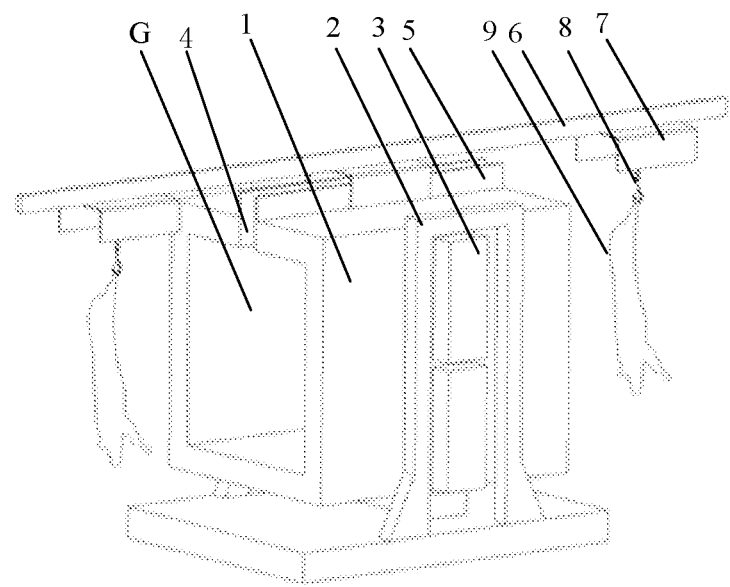
FIG. 1 is an overall schematic diagram of a static CT detection device involved in an embodiment of the present disclosure.

Features and exemplary embodiments of various aspects of the present disclosure will be described in detail below. In order to make the purpose, technical solutions and advantages of the present disclosure more clear, the present disclosure will be further described in detail below with reference to the accompanying drawings and specific embodiments. It should be understood that the specific embodiments described herein are only intended to explain the present disclosure, and are not intended to limit the present disclosure. It will be apparent to the person skilled in the art that the present disclosure may be practiced without some of these specific details. The following description of the embodiments is merely to provide a better understanding of the present disclosure by illustrating examples of the present disclosure.

According to the configuration of the static CT detection device according to the one aspect of the present disclosure, due to the providing of the opening portion, the static CT detection device can be combined with a production line device, and the object under detection is conveyed by the production line device, and thus the conveying belt is not needed, the operation of moving the object under detection onto the conveying belt is not required either, and the work efficiency is improved.

In the static CT detection device of above configuration, a conveying member for carrying the object under detection to pass through the detection channel protrudes toward the detection channel through the opening portion.

The static CT detection device of above configuration further includes a shielding cover driven by a driving part together with the conveying member, and the shielding cover covers the opening portion when the conveying member passes through the opening portion.

According to the above configuration, by providing the shielding cover, the rays in the detection channel can be effectively prevented from being radiated to the outside.

In the static CT detection device of above configuration, the object under detection does not come into contact with the shielding body when it is carried by the conveying member and passes through the detection channel.

According to the above configuration, it can effectively prevent the shielding body from being contaminated due to contact between the object under detection and the shielding body.

In the static CT detection device of the above configuration, the opening portion is located at a top of the shielding body.

According to the above configuration, it can effectively detect the object under detection that is conveyed on a hanging production line device by the static CT detection device.

In the static CT detection device of the above configuration, the ray source is composed of at least one of a distributed ray source and a single-spot ray source, and on one or more planes orthogonal to a direction in which the object under detection is conveyed along the detection channel, the ray source is arranged outside the detection channel and around a portion of the detection channel other than the opening portion.

In the static CT detection device of the above configuration, on one or more planes orthogonal to a direction in which the object under detection is conveyed along the detection channel, the detector is arranged outside the detection channel, around a portion of the detection channel other than the opening portion and corresponding to the ray source.

The static CT detection device of the above configuration further includes upright shielding walls disposed on two sides of the opening portion and erected along a direction orthogonal to the shielding body, and the shielding cover covers the upright shielding walls when passing through the opening portion.

According to the above configuration, by providing the labyrinth-shaped cover at the opening of the shielding body, radiation of the rays to the outside can be more effectively prevented.

In the static CT detection device of the above configuration, wherein the object under detection is meat material.

According to the above configuration, the meat material can be detected without being contacted, thus avoiding the contact between the meat material and the detection device, and reducing the risk of cross-contamination. Further, in the case that the meat material is conveyed for detection in a hanging manner, the detection accuracy can be improved. Furthermore, in the case that the meat material is not in contact with the detection device, the device is less contaminated, reducing the frequency of cleaning.

According to the static CT detection device of the present disclosure, since the static CT detection device can be effectively matched with the production line device, manual operations are reduced, and the production cost is reduced.

Figure 2:
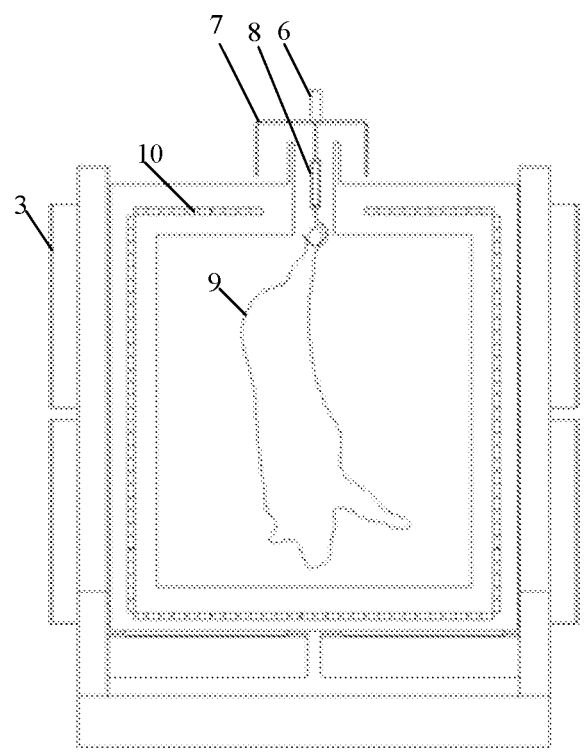
FIG. 2 is a cross-sectional view of a static CT detection device involved in an embodiment of the present disclosure.

As an embodiment, FIG. 1 is an overall schematic diagram of a static CT detection device according to an embodiment of the present disclosure. FIG. 2 is a cross-sectional view of a static CT detection device according to an embodiment of the present disclosure, taken along a direction perpendicular to a conveying direction of a movement channel shown in FIG. 1. A detailed description will be given with reference to FIG. 1 and FIG. 2.

The static CT detection device includes a shielding body 1, a frame 2, a ray source 3 and a detector 10. The shielding body 1 surrounds and forms a detection channel G through which an object under detection can pass. The shielding body 1 is supported by the frame 2, and certainly, the frame 2 may be not provided and the shielding body 1 is directly placed on the floor. The ray source 3 emits rays for detecting the object under detection when the object under detection passes through the detection channel G. The detector 10 acquires the rays emitted by the ray source 3 and having passed through the detection channel G. The shielding body 1 is formed with an opening portion 4 extending from an inlet of the detection channel G to an outlet of the detection channel G.

In the present embodiment, the description is made by taking a meat material 9 as the object under detection.

The shielding body 1 is provided with the opening portion 4 at a top thereof. The meat material 9 usually hangs in a production line for convey, detection and processing. As shown in FIG. 1, the components for conveying the meat material 9 include a production line 6, a hanging part 8 and a driving part not shown. The production line 6 is disposed above the opening portion 4 of the static CT detection device. The hanging part 8 that carries the meat material 9 to pass through the detection channel G, protrudes toward the detection channel G through the opening portion 4.

When the driving parts (not shown) works, the hanging part 8 is driven to carry the meat material 9 to move, and when passing above the static CT detection device, the hanging part 8 protrudes into the detection channel G through the opening portion 4, and simultaneously carries the meat material 9 to move from inlet of the detection channel G toward the outlet of the detection channel G. The meat material 9 does not come into contact with the shielding body 1 when it is carried by the hanging part 8 and passes through the detection channel G, and the meat material 9 is not supported or carried by the shielding body 1. When the meat material 9 passes through a position corresponding to the ray source 3, the ray source 3 emits the rays to detect the meat material 9. Moreover, the detector opposite and corresponding to the ray source 3 acquires the rays incident to the interior of the detection channel G, and performs detection.

By providing the opening portion 4 in the shielding body 1, the static CT detection device can be highly integrated with the production line, and an additional conveying device is not required. In the present embodiment, the operation of moving the meat material 9 onto the conveying belt is not needed, the meat material 9 is directly carried into the detection device through the production line, and thus the time required for the detection of the meat material 9 can be saved, and the detection and processing of the meat material 9 can be completed conveniently in the production line. Further, when detecting the meat, there is no need to insert a detecting device into the meat, a non-contact detection of the meat can be realized, and the risk of cross-contamination can be avoided. Furthermore, in the present embodiment, since the meat material 9 does not contact with the shielding body 1, the contamination of the static CT detection device can be reduced, the interior of the static CT detection device can be kept clean, and the number of cleanings can be reduced. In addition, in the present embodiment, the sorting can be realized in the production line instead of manual work.

Optionally, as an embodiment, the static CT detection device further includes a shielding cover 7, which moves along the production line 6 together with the hanging part 8 under driving of the driving part (not shown). When the hanging part 8 passes through the opening portion 4 of the static CT detection device, the shielding cover 7 covers the opening portion 4. Therefore, the rays in the detection channel G can be effectively prevented from being radiated out.

Figure 3:
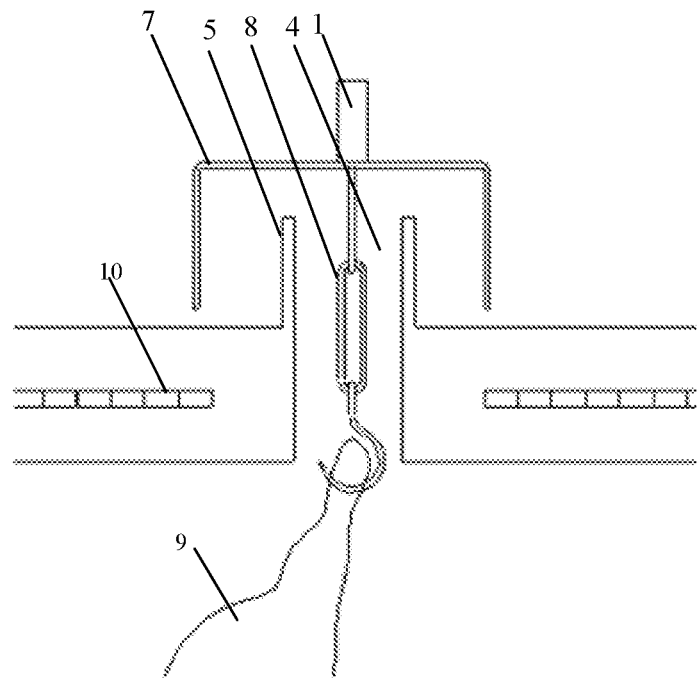
FIG. 3 is a cross-sectional view of a labyrinth cover of a static CT detection device according to an embodiment of the present disclosure.

Optionally, as an embodiment, the static CT detection device further includes upward shielding walls 5, and FIG. 3 is a cross-sectional view of a labyrinth cover of the static CT detection device. The upright shielding walls 5 are erected on two sides of the opening portion 4 in a direction orthogonal to the shielding body 1, and the shielding cover 7 covers the upright shielding walls 5 when passing through the opening portion 4. Therefore, by providing the upright shielding walls 5 to form a labyrinth-like shielding structure together with the shielding cover 7, the rays in the detection channel G can be effectively prevented from being radiated to the outside.

Figure 4:
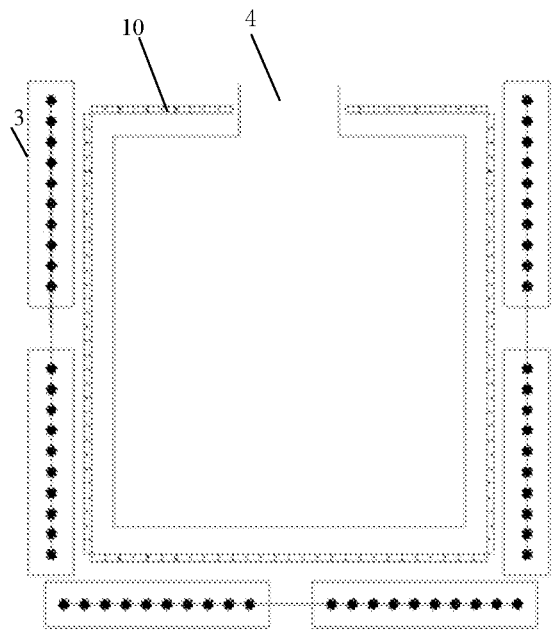
FIG. 4 is a schematic diagram of an example of configuration of a ray source and a detector of a static CT detection device according to an embodiment of the present disclosure.

The ray source and detector involved in the above embodiments will be described in detail below. FIG. 4 is a schematic diagram of an example of configuration of a ray source and a detector of a static CT detection device according to an embodiment of the present disclosure.

In the present embodiment, the ray source includes a plurality of distributed ray sources, and the distributed ray sources are arranged outside the detection channel and around a portion of the detection channel other than said opening portion, on a plane orthogonal to a direction in which the object under detection is conveyed along the detection channel. The distributed ray sources here can be set continuously or discontinuously. As shown in FIG. 4, several distributed ray sources are connected end to end to form the ray source. That is, the ray source 3 includes a plurality of distributed ray sources, and the plurality of distributed ray sources are provided on a same plane orthogonal to the direction in which the object under detection is conveyed along the detection channel, and are provided in the portion other than the opening portion. Certainly, the plurality of distributed ray sources further can be arranged on multiple different planes orthogonal to the direction in which the object under detection is conveyed along the detection channel, and for example, projections of the plurality of distributed ray sources arranged on multiple different planes on one same plane of said planes are connected end to end. FIG. 4 shows an arrangement scheme of 6 groups of ray sources. Each distributed ray source includes several spot ray sources. Each spot ray source emits a fan-shaped X-ray in a controllable state, and the X-ray can cover a part of the scanning channel. The scanning angle of the distributed ray source to any point in the channel meets the CT reconstruction imaging requirements, such as more than 180°. The distributed ray sources are arranged according to coverage length of target spots and the size of a single ray source required for CT reconstruction imaging.

Figure 5:
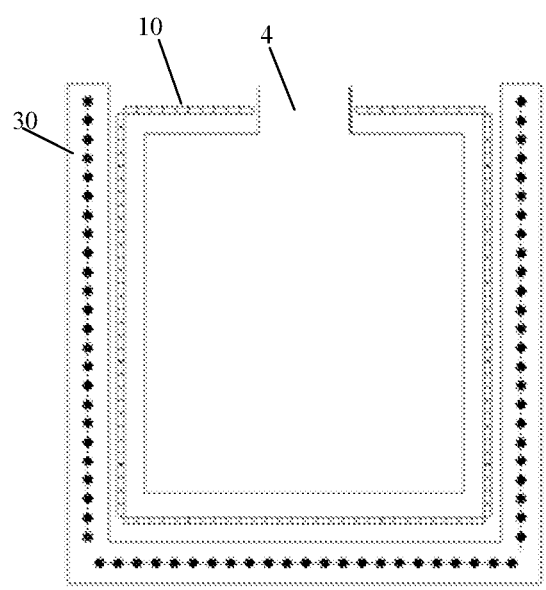
FIG. 5 is a schematic diagram of another example of configuration of a ray source and a detector of the static CT detection device according to the embodiment of the present disclosure.

FIG. 5 is a schematic diagram of another example of the configuration of the ray source and the detector of the static CT detection device according to the embodiment of the present disclosure. In the present embodiment, a polygonal distributed ray source 30 is used.

As shown in FIGS. 4 and 5, on a plane orthogonal to the direction in which the object under detection is conveyed along the detection channel, the detector 10 is arranged outside the detection channel, around a portion of the detection channel other than the opening portion and corresponding to the ray source. The detector here can be set continuously or discontinuously. The detector 10 acquires the rays emitted from the ray source on an opposite direction and having passed through the detection channel. A detector ring formed by the detector around the shielding body and a ray source ring formed by the ray source around the shielding body are offset from each other by a certain distance in a direction of the detection channel, so that the detector will not block the rays emitted by the ray source behind it.

In the above-mentioned embodiments, the description is made by taking a rectangular detection channel as an example, but the present disclosure is not limited to this. The shape of the detection channel can be made into any shape such as ellipse and other polygons according to the requirements of the object under detection. The height and width of the detection channel can be designed to be different according to requirements. When the size of the detection channel is different, the number of detectors and ray sources can be increased or decreased according to the size, so that devices of different sizes can share the same ray source and detector components, thereby reducing the cost.

In the above-mentioned embodiment, the description is made by use of an example in which the position of the opening portion is located at the top of the shielding body, but the present disclosure is not limited to this. Depending on the object under detection and the specific structure of the production line, the opening portion may be provided at positions such as a side or a bottom of the shielding body. Further, the size and structure of the opening portion depend on the specific structure of the production line.

In the above-mentioned embodiments, the target spots of the distributed ray source may be arranged in a straight line, a curved shape or a polygonal shape. According to the shape of the detection channel, the ray source can be arranged in a multi-segment polyline shape or a curved shape. The target spots of the ray source may be arranged continuously and uniformly, or may be arranged discontinuously and non-uniformly. Further, the distributed ray source may be composed of a polyline distributed ray source.

In the above-mentioned embodiment, the description is made by taking an example in which the ray source is the distributed ray source, but the present disclosure is not limited to this. The ray source may further be composed of a combination of single-spot ray sources. In addition, the setting of the single-spot ray sources can be continuous or discontinuous.

In the above-mentioned embodiments, the detectors may also be arranged in a multi-segment polyline shape or a curved shape according to the shape of the detection channel. Further, the detector may be continuously and uniformly arranged, or may be discontinuously and non-uniformly arranged. When part of the scan data is missing due to incomplete detector arrangement, data compensation can be used to make up for the missing, so as to form a complete CT reconstruction image.

In the above-mentioned embodiments, the description is made by taking the detection of the meat material as an example. However, the present disclosure is not limited to the meat material, and it is suitable for any object that needs to be processed on the production line and needs CT detection.

Although the embodiments and specific examples of the present disclosure have been described above in combination with the accompanying drawings, the person skilled in the art can make various modifications and deformations without departing from the spirit and scope of the present disclosure. Such modifications and deformations fall within the scope defined by the appended claims.

What is claimed is:

1. A static CT detection device, comprising:
a shielding body, formed with a detection channel through which an object under detection can pass;
a ray source; emitting rays for detecting the object under detection when the object under detection passes through the detection channel; and
a detector, for acquiring the rays emitted by the ray source and having passed through the detection channel,
wherein the shielding body is formed with an opening portion, and the opening portion extends from an inlet of the detection channel to an outlet of the detection channel,
a conveying member for carrying the object under detection to pass through the detection channel, protrudes toward the detection channel through the opening portion, and
the static CT detection device further comprises a shielding cover driven by a driving part together with the conveying member, and the shielding cover covers the opening portion when the conveying member passes through the opening portion.

2. The static CT detection device according to claim 1, wherein the object under detection does not come into contact with the shielding body when it is carried by the conveying member and passes through the detection channel.

3. The static CT detection device according to claim 2, wherein the object under detection is meat material.

4. The static CT detection device according to claim 1, wherein the opening portion is located at a top of the shielding body.

5. The static CT detection device according to claim 4, wherein the object under detection is meat material.

6. The static CT detection device according to claim 1, wherein the ray source is composed of at least one of a distributed ray source and a single-spot ray source, and on one or more planes orthogonal to a direction in which the object under detection is conveyed along the detection channel, the ray source is arranged outside the detection channel and around a portion of the detection channel other than the opening portion.

7. The static CT detection device according to claim 6, wherein the object under detection is meat material.

8. The static CT detection device according to claim 1, wherein on one or more planes orthogonal to a direction in which the object under detection is conveyed along the detection channel, the detector is arranged outside the detection channel, around a portion of the detection channel other than the opening portion and corresponding to the ray source.

9. The static CT detection device according to claim 8, wherein the object under detection is meat material.

10. The static CT detection device according to claim 1, further comprising upright shielding walls disposed on two sides of the opening portion and erected along a direction orthogonal to the shielding body, and
the shielding cover covers the upright shielding walls when passing through the opening portion.

11. The static CT detection device according to claim 10, wherein the object under detection is meat material.

12. The static CT detection device according to claim 1, wherein the object under detection is meat material.

\* \* \* \* \*